United States Patent

Heim et al.

[11] Patent Number: 4,617,924
[45] Date of Patent: Oct. 21, 1986

[54] METHOD AND APPARATUS FOR ARTIFICIAL RESPIRATION AND THE MEASUREMENT OF BREATHING GAS VALUES

[75] Inventors: Ulrich Heim, Reinfeld; Peter Gebhardt, Stockelsdorf, both of Fed. Rep. of Germany

[73] Assignee: Drägerwerk AG, Fed. Rep. of Germany

[21] Appl. No.: 693,016

[22] Filed: Jan. 18, 1985

[30] Foreign Application Priority Data

Jan. 20, 1984 [DE] Fed. Rep. of Germany ....... 3401841

[51] Int. Cl.$^4$ ........................................... A61M 16/00
[52] U.S. Cl. .......................... 128/204.23; 128/204.25
[58] Field of Search ..................... 128/203.14, 203.25, 128/204.18, 204.21, 204.22, 716, 718, 719, 204.25

[56] References Cited

U.S. PATENT DOCUMENTS

| | | | |
|---|---|---|---|
| 3,799,149 | 3/1974 | Rummel et al. ..................... | 128/718 |
| 3,894,536 | 7/1975 | Tysk ................................ | 128/205.24 |
| 4,345,612 | 8/1982 | Koni et al. ....................... | 128/203.14 |
| 4,444,201 | 4/1984 | Itoh ................................ | 128/204.23 |
| 4,481,944 | 11/1984 | Bunnel ............................ | 128/204.18 |
| 4,508,117 | 2/1985 | Rodari ............................ | 128/204.25 |

Primary Examiner—Henry J. Recla
Attorney, Agent, or Firm—McGlew and Tuttle

[57] ABSTRACT

A ventilating system includes a high frequency controlled breathing gas source in HFJV operation, wherein the exhaled gas is removed through an outlet line through which a flush gas is conducted, is improved to permit a determination, under high frequency ventilation, of both the final expiratory $CO_2$ concentration and the basic pressure building up in the lungs (the lung-internal PEEP). To this end, the control device is in addition connected to a flush gas valve provided upstream of the breathing gas supply device, and designed to intercalate a measuring interval after a sequence of breathing gas pulses, during which interval the breathing gas valve and the flush gas valve are closed. A system of measuring the breathing gas valves is provided in the outlet line and it is actuated during the measuring interval to perform the measuring operation.

10 Claims, 2 Drawing Figures

METHOD AND APPARATUS FOR ARTIFICIAL RESPIRATION AND THE MEASUREMENT OF BREATHING GAS VALUES

FIELD AND BACKGROUND OF THE INVENTION

This invention relates in general to respirators and in particular to a new and useful method and apparatus for controlling the flow of breathing gas to a patient and for creating a measuring interval during the respiration in which various breathing gas characteristics are determined.

Substantial problems arise in the monitoring of an artificial respiration with a quick and accurate determination of breathing gas values and ventilation parameters, especially if a high frequency pulse method where a jet nozzle (High Frequency Jet Ventilation or HFJV) is used.

German Pat. No. 20 47 659 discloses a ventilation system wherein the breathing gas source in HFJV operation produces high-pressure gas-pulses having a pulse recurrence frequency in excess of 600 per minute, and alternately pulse trains and pauses therebetween are provided. The pauses are intended as intervals for examining gas samples. The gas samples are analyzed in a respective device and depending on the result, the control of the ventilation can be adjusted to obtain the best respiration pattern.

The $CO_2$ concentration, i.e. $CO_2$ content in the exhaled air, which is measured at the end of an expiration phase to determine the partial pressure of $CO_2$ in the blood, is a generally acknowledged important control variable in conventional ventilation (Intermittent Positive Pressure Ventilation or IPPV) without a pulse control. While in a conventional ventilation, the determination of the $CO_2$ content of the exhaled air is not particularly difficult, during high-frequency ventilation, the $CO_2$ determination is not so easy. The exhaled gas is strongly diluted by the continuous flow of flush gas, and because of the minimum volumina per stroke during the high-frequency ventilation, which are on the order of magnitude of the dead space of the breathing gas supply device the $CO_2$ concentration in the exhaled gas does not correspond to that of the alveolar region.

Another problem in high-frequency ventilation of a patient is the determination of the constant basic pressure established in the lungs, the so called "lung-internal PEEP". At high ventilation frequencies, about in the range of 600 per minute, such as usual in this kind of ventilation, the so called "air trapping" builds up a pressure in the lungs, which does not decay at the end of the short expiration phases. With methods hitherto known, this internal PEEP (Positive End Expiratory Pressure) cannot be measured with satisfactory accuracy.

A prior art qualitative measurement utilizes thorax bloating for inferring therefrom the pressure built up in the lungs. To this end, the thorax impedance can be determined in a known manner through electrodes applied to the chest, or strain bands placed on the chest, extending and thus providing resistance values to be measured. Such measurements furnish only coarse information on the lung-internal PEEP and the fixing of measuring elements or bands may be difficult, particularly with a traumatic chest.

SUMMARY OF THE INVENTION

The invention is directed to a system of the above mentioned which permits the determination during a high-frequency ventilation of the expiratory $CO_2$ concentration and thus the $CO_2$ partial pressure in the blood, and in addition to quantitatively determine from the exhaled air the lung-internal PEEP i.e. the basic pressure building up in the lungs during HFJV.

This is obtained by providing that the controller is connected to a flush gas valve provided upstream of the breathing gas supply device and is so designed that after a sequence of breathing gas pulses, a measuring interval is intercalated during at least part of which the breathing gas valve and the flush gas valve are closed, and that at least one system for measuring breathing gas values is provided in the outlet line which is put in operation during the measuring interval to determine the measured values. The breathing gas valve and the flush gas valve are not necessarily simultaneously closed during the entire measuring interval, since a control displaced in phase with these valves may be advisable in certain applications, even though in any case with an overlapping in the measuring interval.

Developments of the invention include special design of the measuring system as a $CO_2$ analyzer and flowmeter, and arrangements with a multiplier in addition, with the possibility of determining the total inhaled $CO_2$ amount for a longer period of time, or the $CO_2$ production per unit time, through an integrator controlled by the controller.

To determine the $CO_2$ concentration in such a ventilating system, first, by correspndingly controlling the breathing gas valve, the high-frequency ventilation is interrupted and, prior to starting the measuring interval, transformed into a conventional breathing pattern. This may advantageously be obtained by correspondingly extending the pulse duration and reducing the pulse spacing, in a way so as to produce long strokes similar to the conventional positive excess pressure duration (IPPV). This is to make sure that the $CO_2$ concentration in the expiration gas examined during the measuring interval corresponds to the alveolar $CO_2$ concentration. After the last bloating caused by the breathing gas supply, the control device switches the breathing gas valve and the flush gas valve into closed positions, so that only expiration gas now flows in the outlet line, having a $CO_2$ concentration which corresponds to the alveolar $CO_2$ concentration. The measuring system connected to the outlet line, in the present example includes a $CO_2$ analyzer, which is then instructed to perform the measuring operation.

To determine the lung-internal PEEP, the high frequency ventilation is interrupted by closing the breathing gas valve and the flush gas valve for a period of time corresponding to several high-frequency pulse cycles, and at the same time, after the last high-frequency pulse, the expiration gas flow is measured with a flowmeter and integrated by means of an integrator connected to the flowmeter, until the flow drops to zero.

The value of the integral up to the point at which, with a continuous high-frequency pulse train, the next high-frequency pulse would have started, corresponds to the tidal volume in the high-frequency ventilation; the total integral minus the tidal volume corresponds to the basic bloating. With the known compliance of the lungs this value can be used for computing the internal PEEP.

Since the compliance of the lungs may vary during long term ventilation, it is advisable to determine the compliance value shortly before or after measuring the expiration volume as described above. In the concerned ventilating system and analogously to the above mentioned measuring process, the compliance may be measured to determine the end expiratory $CO_2$ concentration.

To this end, a conventional breathing stroke is produced with the jet nozzle, while selecting a long inspiration time to obtain a definite pressure level (plateau). Upon reaching this predetermined pressure level, the pressure present in the upper portion of the respiratory tract is measured by means of a pressure pickup provided in the breathing gas supply device, at a location remote from the orifice of the jet nozzle. During the following expiration phase, and in the same way as in the determination of the expiratory $CO_2$ concentration, the breathing gas flow to the jet nozzle is interrupted through the breathing gas valve and the flush gas flow is interrupted through the flush gas valve, so that with a corresponding triggering of the integrator, the expiration volume can be determined by means of the flowmeter in the outlet line.

From the measured plateau pressure and the expiration value, the actual compliance of the lungs and thus, as mentioned above, the lung-internal PEEP, can be computed.

What is substantial in the inventive arrangement is the provision of a control flush gas valve, in addition to the high-frequency controlled breathing gas valve producing the breathing gas pulses. This makes it possible to obtain reliable values of the alveolar $CO_2$ concentration, the lung-internal PEEP, and the actual compliance in a manner that is unaffected by the flush gas flow.

In accordance with the invention a breathing gas supply device is supplied with breathing gas through a control valve and it has an opposite end which is connected through the device to the patient. In addition, a flushing gas is connected into the device to provide means for flushing the device of the exhaled air through an outlet. The flushing gas is also controlled by a valve and the controller is connected to the breathing gas valve and the flushing gas valve so as to control their operation and provide a measuring interval for a predetermined period in which the exhaled gas is passed through measuring means such as a $CO_2$ analyzer, pressure sensor or the like during which time the breathing gas and flushing gas supplies are discontinued.

A further object of the invention is to provide a ventilation system which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
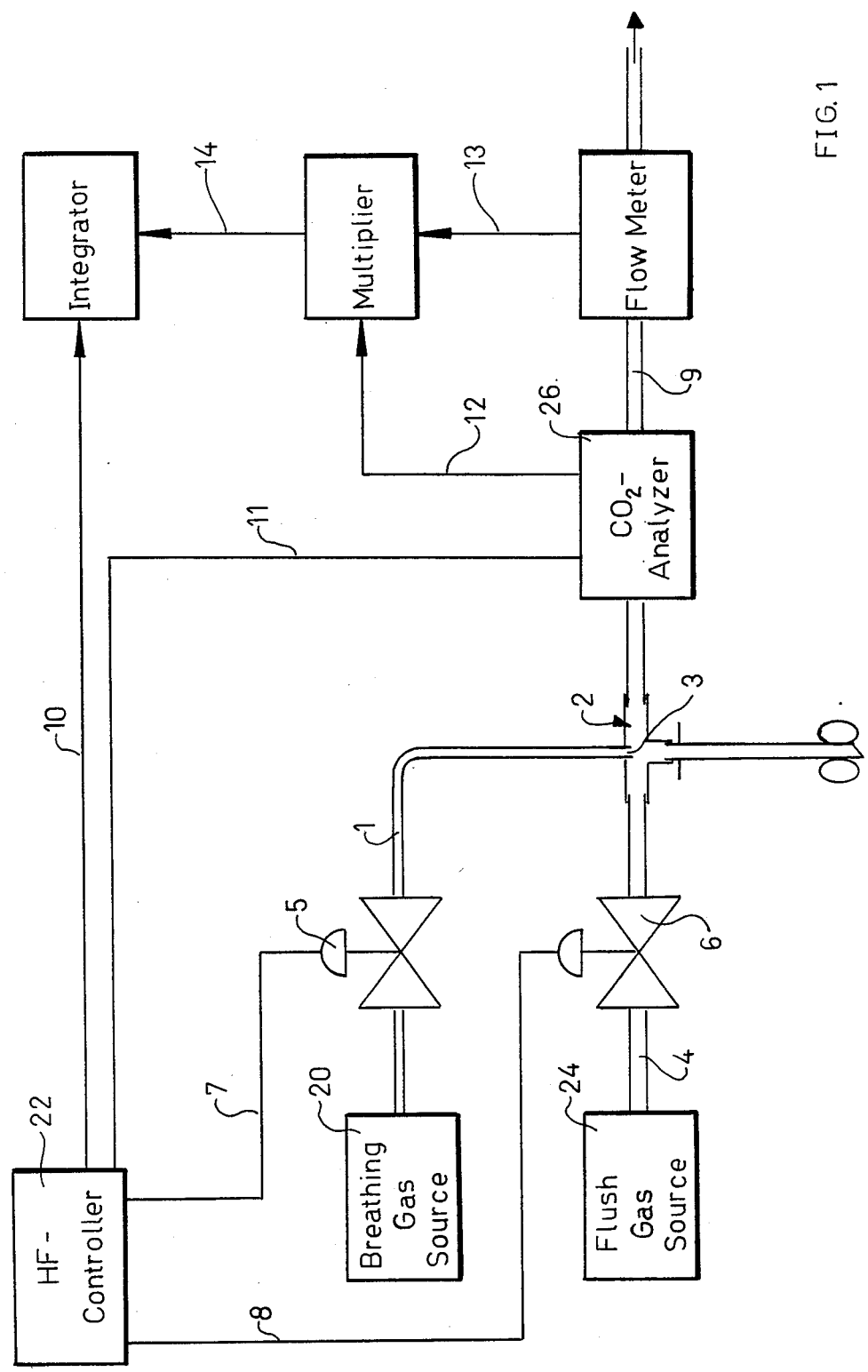
FIG. 1 is a schematic diagram of a ventilation system with controlled breathing gas and flush gas valves, for determining the $CO_2$ concentration, and construction in accordance with the invention.

Referring to the drawings in particular the invention embodied therein in FIG. 1 comprises a ventilating system for breathing apparatus which includes a breathing gas source 20 which supplies breathing gas through a breathing gas supply line to a breathing gas supply device generally designated 2. The gas supply line 1 has a breathing gas control valve 5 therein which is regulated through a control line 7 from a controller 22. A flushing gas supply 24 is connected through a flushing gas supply line 4 to the breathing gas supply device 2 and the flushing gas flow is regulated by a valve 6 which is also controlled by the controller 22 through a control line 8. Flushing gas supply 24 may supply the same gas as breathing gas source 20. The control means or controller 22 provides a measuring interval which provides for the interruption of a supply of breathing gas regulating the valve 5 and flushing gas by regulating the valve 6 for a measuring interval or period in which the exhaled gas is directed through measuring means including the $CO_2$ analyzer 26.

The ventilation source, which may be combined with the breathing gas source, is connected through a flush gas line 4 to the breathing gas supply device 2. In the supply line 1, the breathing gas valve 5 controllable at high frequency is provided. In the flush gas line 4, the controllable flush gas valve 6 is provided.

Breathing gas valve 5 and flush gas valve 6 are controlled through the high-frequency controller 22 which is connected to these valves through control lines 7,8.

Measuring means comprising a $CO_2$ analyzer 26 and a flowmeter are provided in an outlet line 9 leading outwardly from gas supply device 2.

Signal lines 10 and 11 connect the high-frequency controller to an integrator and to the $CO_2$ analyzer. Output lines 12,13 from the $CO_2$ analyzer and the flowmeter are applied to a multiplier whose output is connected through a line 14 to the integrator.

In this circuit arrangement, the ventilating system with the two controllable valves 5,6 serves the purpose of determining the alveolar $CO_2$ concentration.

Figure 2:
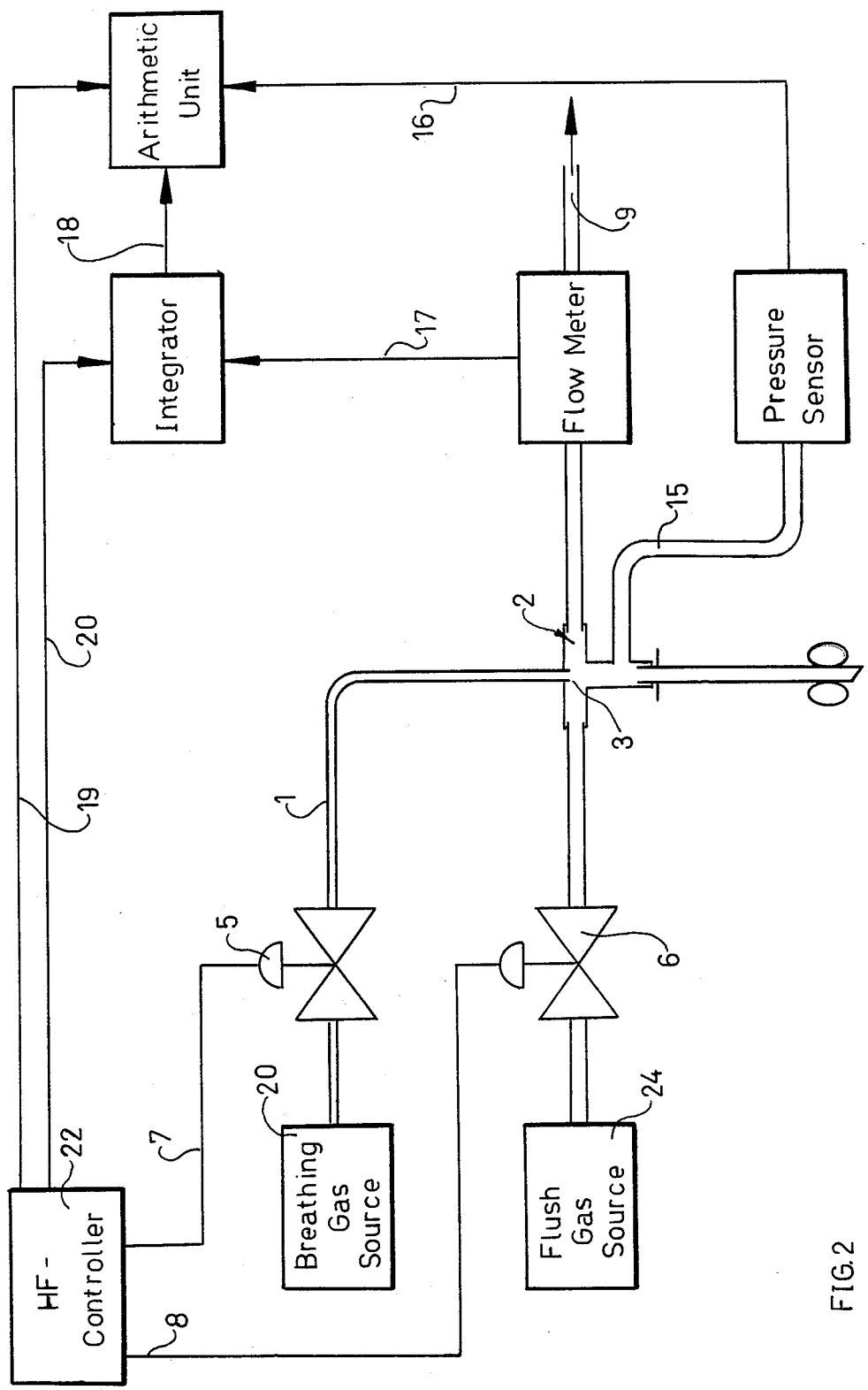
FIG. 2 illustrates a similar system for determining the lung-internal PEEP.

In the arrangement of FIG. 2, the substantial parts of the system, namely the breathing gas source, the flush gas source, the high-frequency controller, the controllable valves for the breathing gas and the flush gas, and the breathing gas supply device, are maintained without change.

In the breathing gas supply device 2, at a location remote from the orifice of the jet nozzle 3, a line 15 is connected leading to a pressure sensor whose output is applied to an arithmetic unit. The output of the flowmeter is connected through a line 17 to the integrator which also is connected, through a signal line 18, to the arithmetic unit. This unit is in addition connected, through another signal line 19, to the high-frequency controller. Another signal line 20 connects the high-frequency controller to the integrator.

While specific embodiments of the invention have been shown and described in detail to illustrate the application of the principles of the invention, it will be understood that the invention may be embodied otherwise without departing from such principles.

What is claimed is:

1. A ventilating system comprising a breathing gas source for supplying a flow of breathing gas, a breathing gas supply line having one end connected to said breathing gas source and having an opposite end with a jet nozzle, a breathing gas supply device having one end connected to said opposite end of said breathing gas supply line for receiving the flow of breathing gas over said jet nozzle, a flushing gas line connected into said breathing gas supply device, an always open outlet line connected into said breathing gas supply device, said breathing gas supply device having an end for connection to a patient, a breathing gas valve in said breathing gas line for regulating the breathing gas flow to said breathing gas supply device, a flush gas valve in said flushing gas line for regulating the flow of flushing gas to said breathing gas supply device and to said outlet line, and control means connected to said breathing gas valve and said flushing gas valve for providing the flow of breathing gas through said breathing gas valve in high frequency pulses for a predetermined period and said flushing gas through said flushing gas valve for a predetermined period and providing a measuring interval in which said breathing gas valve and said flushing gas valve are closed, and measuring means connected to said outlet for measuring breathing gas values during the measuring interval.

2. A ventilating system according to claim 1, wherein said measuring means comprises a $CO_2$ analyzer.

3. A ventilating system according to claim 2, including a multiplier connected to said $CO_2$ analyzer and a flowmeter connected to said $CO_2$ analyzer, an integrator connected to the output of said multiplier and a signal line connected between said control means and said multiplier.

4. A ventilating system according to claim 1, including a flowmeter in said outlet line.

5. A ventilating system according to claim 4, including an integrator connected to said flowmeter, a signal line connecting said integrator to said control means, a pressure sensor connected to said breathing gas supply device, an arithmetic unit connected to said pressure sensor, a signal line connected between said arithmetic unit and said integrator and a signal line connected between said control means and said integrator.

6. A ventilating system according to claim 5, wherein said pressure sensor is connected to said breathing gas supply device at a location remote from the connection of said breathing gas supply line and from said supply device, said breathing gas jet nozzle.

7. A ventilating system according to claim 1, wherein said control means has means which effects the measuring interval at predetermined periodic recurring times.

8. A ventilating system according to claim 1, wherein said control means has means which effects prior to the start of a measuring interval, the duration of a breathing gas pulse and the pulse duration to spacing ratio and provides means for modifying them to obtain a conventional breathing pattern.

9. A method of effecting the respiration of a patient comprising:
supplying breathing gas in high frequency pulses and over a jet nozzle to a breathing gas supply device;
supplying flushing gas to the breathing gas supply device;
connecting the breathing gas supply device to a patient for supplying the patient with the high frequency pulses of breathing gas and with the flushing gas;
interrupting the supply of high frequency breathing pulses as well as the supply of flushing gas during a measuring interval, the patient exhaling through the breathing gas supply device during the measuring interval into an outlet connected to the breathing gas supply device that is always open; and
measuring at least one parameter of gas in the outlet during the measuring interval.

10. A method according to claim 9, in which a measuring interval is provided after discontinuing the supply of breathing gas and flushing gas and wherein the exhaled gas is directed through a $CO_2$ analyzer through a flowmeter and the indications of the flowmeter and the $CO_2$ analyzer are given to an integrator wherein control means are connected to the breathing gas supply and the flushing gas supply for discontinuing the supplies during a measuring interval during the respiration.

* * * * *